United States Patent [19]

Bühring

[11] Patent Number: 5,777,140

[45] Date of Patent: Jul. 7, 1998

[54] PROCESS FOR THE PREPARATION OF ACYLOXYALKANESULFONATES HAVING IMPROVED PROPERTIES

[75] Inventor: Dirk Bühring, Brasil, Germany

[73] Assignee: Hoechst Aktiengesellschaft, Frankfurt, Germany

[21] Appl. No.: 624,884

[22] Filed: Mar. 27, 1996

[30] Foreign Application Priority Data

Mar. 29, 1995 [DE] Germany .................. 195 11 459.0

[51] Int. Cl.⁶ ................................................ C07C 303/22
[52] U.S. Cl. .................................... 554/92; 560/266
[58] Field of Search ............................ 554/92; 560/266

[56] References Cited

U.S. PATENT DOCUMENTS 5,384,421 1/1995 Day et al. .................... 554/92
5,473,089 12/1995 Gutsche et al. ............... 554/92

*Primary Examiner*—Robert Gerstl
*Attorney, Agent, or Firm*—Connolly and Hutz

[57] ABSTRACT

Process for the preparation of acyloxyalkanesulfonates having improved properties The acyloxyalkanesulfonates are obtained in accordance with the invention by direct esterification in which at least one fatty acid is esterified with at least one ammonium hydroxyalkanesulfonate of the formula $HO\text{-}A\text{-}SO_3^{-+}NR^1R^2R^3R^4$ in which A is a $C_2\text{–}C_4$-alkylene and $R^1_1$, $R^2_1$, $R^3$ and $R^4$ are hydrogen or a $C_1\text{–}C_4$-alkylene group in the presence of an esterification catalyst at a temperature of not more than 200° C., with removal of the water present. This process gives a product of high acyloxyalkane-ammonium sulfonate content without the need for a consistency regulator to be added.

8 Claims, No Drawings

5,777,140

PROCESS FOR THE PREPARATION OF ACYLOXYALKANESULFONATES HAVING IMPROVED PROPERTIES

The invention relates to a process for the preparation of acyloxyalkanesulfonates having improved properties by esterification of fatty acids with hydroxyalkanesulfonates.

Acyloxyalkanesulfonates are valuable anionic surfactants which are employed in particular in the preparation of syndet soaps, cosmetic compositions and cleaning formulations. They are advantageously prepared by esterifying at least one fatty acid with at least one hydroxyalkanesulfonate (direct esterification). A process of this kind is described, for example, in EP-A-0 585 071 (U.S. Pat. No. 5,384,421). In this process the fatty acid and the salt of the hydroxyalkanesulfonic acid are reacted in the presence of an esterification catalyst and of a consistency regulator at a temperature of from 180° to 240° C., with simultaneous removal of the water present. The consistency regulators employed are certain paraffins. The use of such compounds is necessary since the reaction mixture becomes highly viscous as the esterification proceeds. Although consistency regulators achieve a lower viscosity reaction mixture and facilitate the reaction, the esterification product includes the compounds employed, meaning that the desired acyloxyalkanesulfonate is obtained in a more or less diluted form.

It has now surprisingly been found that the direct esterification under discussion can be carried out without consistency regulators, to give an esterification product having a high content of acyloxyalkanesulfonate, if the fatty acids are esterified with hydroxyalkaneammonium sulfonate and if an esterification temperature of not more than 200° C. is observed. It is an unexpected result that, among the numerous hydroxyalkanesulfonates, it is precisely the ammonium salts of hydroxyalkanesulfonic acids which can be reacted with fatty acids in the absence of consistency regulators. In this way it is possible to prepare highly concentrated acyloxyalkanesulfonates which, as a further unexpected property, possess good solubility in water.

The process according to the invention for the preparation of acyloxyalkanesulfonates having improved properties by esterification of fatty acids with hydroxyalkanesulfonates comprises esterifying a fatty acid of the formula 1 RCOOH (1) in which R is a hydrocarbon radical having 5 to 31 carbon atoms with at least one ammonium hydroxyalkanesulfonate of the formula 2 HO-A-SO$_3^-$ $^+$NR$^1$R$^2$R$^3$R$^4$ (2) in which A is a C$_2$–C$_4$-alkylene and R$^1$, R$^2$, R$^3$ and R$^4$ are identical or different and are hydrogen or a C$_1$–C$_4$-alkyl group in the presence of an esterification catalyst-and in the absence of a consistency regulator at a temperature of not more than 200° C., while removing the water present, to give a product having a high content of acyloxyalkaneammonium sulfonate.

Thus, in the process according to the invention, a selected salt of the hydroxyalkanesulfonic acid is employed, namely an ammonium salt. In the ammonium ion of the following formula 3

(3)

R$^1$ to R$^4$ are hydrogen or a C$_1$–C$_4$-alkyl, preferably methyl or ethyl, and may be identical or different. For instance, the ammonium ion is $^+$NH$_4$ if the radicals R$^1$ to R$^4$ are each hydrogen, or is $^+$NH(CH$_3$)$_3$ or $^+$NH(C$_2$H$_5$)$_3$ if R$^1$ is hydrogen and R$^2$ to R$^4$ are methyl or ethyl. The divalent radical A in the ammonium salt of the given formula 2 to be employed in accordance with the invention is preferably —CH$_2$CH$_2$—, —(CH$_2$)$_3$— or —CH$_2$CH(CH$_3$)—, with particular preference being given to ethylene. Accordingly, the preferred salt in accordance with the invention is ammonium hydroxyethanesulfonate (ammonium isethionate). The ammonium salts can be employed as such but are preferably employed in the form of an aqueous solution, in general as a from 40 to 65% strength by weight solution:

The fatty acid has the formula 1 given above—RCOOH (1)—in which R is a hydrocarbon radical having 5 to 31 carbon atoms, which can be saturated or unsaturated and linear or branched, with preference being given to a linear (unbranched) radical. R can also be a mixture of such hydrocarbon radicals. R is preferably C$_5$–C$_{21}$-alkyl or C$_5$–C$_{21}$-alkenyl or a mixture thereof. The alkyl and alkenyl radicals are preferably unbranched. The alkenyl radicals, furthermore, are preferably mono- to triunsaturated. Examples of fatty acids which may be mentioned are caproic acid, capric acid, lauric acid, myristic acid, stearic acid, arachidic acid, oleic acid, linoleic acid, linolenic acid, coconut fatty acid and tallow fatty acid and mixtures thereof.

The reaction of fatty acid and ammonium hydroxyalkanesulfonate according to the invention is carried out in the presence of a catalyst. Suitable esterification catalysts have been described at length in the abovementioned EP-A-0 585 071, which is incorporated here by reference. They comprise alkanesulfonic acids, hydroxyalkanesulfonic acids, arylsulfonic acids, inorganic acids such as sulfuric acid, phosphoric acid, phosphorous acid, boric acid or anhydrides thereof, heavy metal salts, such as zinc sulfate, zirconium sulfate, zinc isethionate, zinc borate, aluminum sulfate, titanium sulfate or tungsten phosphate, metal oxides, such as zinc oxide, aluminum oxide, magnesium oxide, cerium oxide, zirconium oxide or lanthanum oxide, and also mixtures of two or more of the abovementioned catalysts, and soaps formed from heavy metals and metal oxides. A particularly preferred esterification catalyst is zinc oxide. The esterification catalyst is employed in a quantity of in general from 0.05 to 2% by weight, preferably from 0.05 to 1% by weight, percentages by weight being based on fatty acid and hydroxyalkanesulfonic acid ammonium salt.

The reaction of fatty acid and hydroxyalkanesulfonic acid ammonium salt, generally in the molar ratio of from 1:1 to 2:1,preferably about 1:1,is carried out according to the invention at a temperature of not more than 200° C.; in other words, during the entire reaction the temperature is not to rise above 200° C. The preferred temperature range is from 170° to 200° C., and the particularly preferred range from 180° to 190° C. The water which may be introduced into the reaction mixture with the starting components, and the water produced by the esterification reaction, is discharged continuously from the reaction mixture. Because of the specific hydroxyalkanesulfonic acid salt employed, the reaction mixture remains homogenous and of relatively low viscosity, and can readily be stirred, up to the end of the reaction, even at 100% conversion; no consistency regulator is required. The time taken to reach the desired conversion of fatty acid or of ammonium hydroxyalkanesulfonate is from about 4 to 8 hours. In general the aim will not be for 100% conversion, for example for reasons of time, but instead the esterification reaction will be terminated at a lower percentage, for example at from 75 to 90% by weight acyloxyalkaneammonium sulfonate.

In detail, the process according to the invention can be carried out, for example, by introducing—at atmospheric pressure—the fatty acid, the ammonium salt of the hydroxyalkanesulfonic acid and the esterification catalyst into a reaction vessel and heating the mixture with stirring to the temperature indicated. Water present is distilled off even while heating the reaction mixture, and this process takes place continuously during the esterification reaction. The process according to the invention can also be carried out in accordance with the method described in EP-A-0 585 071. In this case, the esterification reaction is carried out partly at atmospheric pressure and partly with application of a vacuum, in order to discharge the water more rapidly. After the desired degree of conversion has been reached, the esterification reaction is terminated, for example by cooling. The reaction product obtained is liquid or solid at room temperature. When the product is solid at room temperature it can be processed using, for example, a flaking roll or a cooling belt. With regard to the compound ammonium hydroxyalkanesulfonate, which like the other components is known and commercially available, the following comments may be made: ammonium salts of hydroxyalkanesulfonic acids can be prepared by neutralizing, for example, isethionic acid with ammonia or with an amine, or by reacting an amine with sulfur dioxide and with an alkylene oxide in aqueous solution, as shown by the equation below, using trimethylamine as the amine compound and ethylene oxide as the alkylene oxide compound:

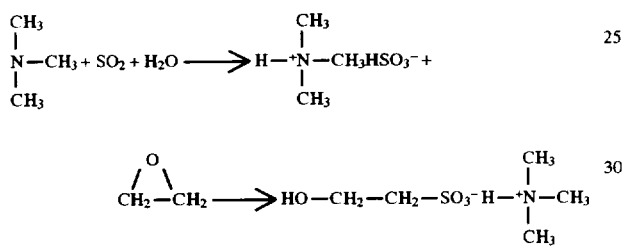

With the process according to the invention, which can also be carried out on the industrial scale, it is possible to prepare concentrated ammonium acyloxyalkanesulfonates. As further advantageous properties, these salts have better solubility in water than other salts and a good feel on the skin. The products obtained in accordance with the invention are therefore suitable in particular for aqueous formulations as well. Because of the direct esterification (direct condensation) it is possible to dispense with the use of fatty acid chlorides, which would otherwise have to be prepared in a separate step from fatty acid. The use of consistency regulators and/or diluents, which in general are not value substances for cleaning formulations and cosmetic compositions, for example, is not necessary. In the process according to the invention, therefore, the reaction mixture essentially consists only of fatty acid, ammonium hydroxyalkanesulfonate and esterification catalyst. As mentioned above, the solid or liquid reaction product generally comprises from 75 to 90% by weight acyloxyalkaneammonium sulfonate, based on the total solid or liquid product. The ammonium salts of acyloxyalkanesulfonic acids which are obtained in accordance with the invention have the following formula 4

  (4)

in which R, A and $R^1$ to $R^4$ are as defined.

The invention will now be illustrated in more detail with reference to examples. Percentages are by weight unless indicated otherwise.

EXAMPLE 1

401 g (2 mol) of lauric acid, 511 g of an aqueous 56% strength ammonium isethionate solution (i.e. 2 mol of ammonium isethionate) and 1.5 g of zinc oxide are placed in a 2 l beaker with ground glass connections, fitted with anchor stirrer, descending distillation bridge, internal thermometer and nitrogen inlet. The mixture is heated to 190° C. and held at this temperature. The water introduced into the mixture and the water formed during the direct condensation is distilled off continuously. The reaction is terminated at an ammonium lauroylisethionate content of 86% and the reaction product is poured onto a metal plate for cooling. This product essentially consists of 86% ammonium lauroylisethionate, 8% lauric acid and 6% ammonium isethionate.

EXAMPLE 2

436 g (2 mol) of coconut fatty acid with an average molecular weight of 218, 596 g of an aqueous 48% strength ammonium isethionate solution (i.e. 2 mol of ammonium isethionate) and 1.5 g of zinc oxide are placed in a 3 l beaker with ground glass connections, fitted with anchor stirrer, descending distillation bridge, internal thermometer and nitrogen inlet. The mixture is heated to 180° C. and held at this temperature. The water introduced into the mixture and the water formed during the direct condensation is distilled off continuously. The reaction is terminated at an ammonium cocoylisethionate content of 90%. The reaction mixture is cooled to 145° C. and is poured onto a metal plate for cooling. The end product essentially consists of 90% ammonium cocoylisethionate, 5% coconut fatty acid and 5% ammonium isethionate.

EXAMPLE 3

533 g (2.6 mol) of coconut fatty acid with an average molecular weight of 205, 537 g of an aqueous 53% strength ammonium isethionate solution (2 mol of ammonium isethionate) and 1.6 g of zinc oxide are placed in the apparatus of Example 2. The mixture is heated to 180° C. and held at this temperature. The water introduced into the mixture and the water formed during the direct esterification is distilled off continuously. At an ammonium cocoylisethionate content of 80%, reduced pressure (0.5 mbar) is applied and the fatty acid, employed in excess, is distilled off at a continued temperature of 180° C. The reaction product is cooled to 155° C. and poured onto a metal plate for cooling. The product essentially consists of 88% ammonium cocoylisethionate, 8% coconut fatty acid and 4% ammonium isethionate.

EXAMPLE 4

521 g (2.6 mol) of lauric acid, 521 g of an aqueous 55% strength ammonium isethionate solution (2 mol of ammonium isethionate) and 1.6 g of zinc oxide are placed in the apparatus of Example 2. The mixture is heated to 200° C. and held at this temperature, the water present being distilled off continuously. At an ammonium lauroylisethionate content of 75% the reaction is terminated by cooling to room temperature. The reaction product essentially consists of 75% ammonium lauroylisethionate, 20% lauric acid and 5% ammonium isethionate.

EXAMPLE 5

436 g (2 mol) of coconut fatty acid with an average molecular weight of 218, 407 g of an aqueous 53% strength ammonium isethionate solution (1.5 mol of ammonium isethionate) and 1.5 g of zinc oxide are placed in the apparatus of Example 2. The mixture is heated to 180° C. and held at this temperature. The water introduced into the mixture and the water formed during the direct condensation is distilled off continuously. The reaction is terminated at an ammonium cocoylisethionate content of 75%. The reaction product is cooled to 100° C. and poured onto a metal plate for cooling. It consists essentially of 75% ammonium cocoylisethionate, 19% coconut fatty acid and 6% ammonium isethionate.

EXAMPLE 6

218 g (1 mol) of coconut fatty acid having an average molecular weight of 218, 349 g of an aqueous 65% strength triethylammonium isethionate solution (1 mol of triethylammonium isethionate) and 0.8 g of zinc oxide are placed in the apparatus of Example 2. The mixture is heated to 180° C. and held at this temperature, the water present being distilled off continuously. The reaction is terminated at a triethylanmonium cocoylisethionate content of 87% and the reaction product is cooled to 20° C. The liquid reaction product essentially consists of 87% triethylammonium cocoylisethionate, 6% coconut fatty acid and 7% triethylammonium isethionate.

In all the examples, the ammonium acyloxyisethionate content in the reaction product was determined by Epton titration and the fatty acid content by potentiometric titration, while the content of ammonium isethionate was calculated from the conversion.

I claim:

1. A process for the preparation of an acyloxyalkanesulfonate having improved properties by esterification of fatty acids with hydroxyalkanesulfonates, which comprises esterifying at least one fatty acid of the formula 1 RCOOH (1) in which R is a hydrocarbon radical having 5 to 31 carbon atoms with an aqueous solution containing at least one ammonium hydroxyalkanesulfonate of the formula 2 HO-A-SO$_3^-$ $^+$NR$^1$R$^2$R$^3$R$^4$ (2) in which A is a C$_2$–C$_4$-alkylene and R$^1$, R$^2$, R$^3$ and R$^4$ are identical or different and are hydrogen or a C$_1$–C$_4$-alkyl group in the presence of an esterification catalyst and in the essential absence of a consistency regulator by heating the reaction mixture at a temperature of from 170° C. to 200° C., while removing the water present, to give a product having a content of acyloxyalkaneammonium sulfonate of from 75–90%.

2. The process as claimed in claim 1, wherein R is an unbranched C$_5$ to C$_{21}$-alkyl radical, an unbranched C$_5$–C$_{21}$-alkenyl radical or a mixture thereof, A is —CH$_2$CH$_2$—, —(CH$_2$)$_3$— or —CH$_2$CH(CH$_3$)—and R$^1$ to R$^4$ are identical or different and are H, CH$_3$ or C$_2$H$_5$.

3. The process as claimed in claim 1, wherein R is an unbranched C$_5$ to C$_{21}$-alkyl radical, an unbranched C$_5$–C$_{21}$-alkenyl radical or a mixture thereof, A is —CH$_2$CH$_2$— and the ammonium ion $^+$NR$^1$R$^2$R$^3$R$^4$ is $^+$NH$_4$, $^+$NH(CH$_3$)$_3$ or $^+$NH(C$_2$H$_5$)$_3$.

4. The process as claimed in claim 1, wherein the esterification is carried out at a temperature of from 180° to 190° C.

5. The process as claimed in claim 1, wherein the fatty acid and the hydroxyalkanesulfonate are employed in a molar ratio of from 1:1 to 2:1.

6. The process as claimed in claim 1, wherein the fatty acid and the hydroxyalkanesulfonate are employed in a molar ratio of approximately 1:1.

7. The process as claimed in claim 1, wherein the esterification catalyst employed is zinc oxide in a quantity of from 0.05 to 2% by weight, based on fatty acid and hydroxyalkanesulfonate.

8. The process as claimed in claim 1, which comprises esterifying at least one fatty acid of the formula I in which R is an unbranched C$_5$ to C$_{21}$-alkyl radical or an unbranched C$_5$–C$_{21}$-alkenyl radical or a mixture thereof, with at least one hydroxyalkane sulfonate of the formula 2 in which A is —CH$_2$CH$_2$— and $^+$NR$^1$R$^2$R$^3$R$^4$ is $^+$NH$_4$, $^+$NH(CH$_3$)$_3$ or $^+$NH(C$_2$H$_5$)$_3$ in a molar ratio of from 2:1 to 1:1 in the presence of zinc oxide in a quantity of from 0.05 to 1% by weight, based on fatty acid and hydroxyalkanesulfonate, at a temperature of from 170° to 200° C.

* * * * *